(12) United States Patent
Seeman (10) Patent No.: US 9,192,605 B2
(45) Date of Patent: Nov. 24, 2015

(54) COMPOSITIONS AND METHODS FOR TREATING PARKINSON'S DISEASE

(75) Inventor: Philip Seeman, Toronto (CA)

(73) Assignee: CLERA INC., Vancouver, British Columbia (CA)

(*) Notice: Subject to any disclaimer, the term of this patent is extended or adjusted under 35 U.S.C. 154(b) by 642 days.

(21) Appl. No.: 13/386,104

(22) PCT Filed: Jul. 30, 2010

(86) PCT No.: PCT/CA2010/001185
§ 371 (c)(1),
(2), (4) Date: Jan. 20, 2012

(87) PCT Pub. No.: WO2011/011886
PCT Pub. Date: Feb. 3, 2011

(65) Prior Publication Data
US 2012/0115910 A1    May 10, 2012

Related U.S. Application Data

(60) Provisional application No. 61/230,264, filed on Jul. 31, 2009.

(51) Int. Cl.
*A61K 31/4515* (2006.01)
(52) U.S. Cl.
CPC ................... *A61K 31/4515* (2013.01)
(58) Field of Classification Search
CPC .................................... A61K 31/4545
USPC ........................................ 514/327
See application file for complete search history.

(56) References Cited

U.S. PATENT DOCUMENTS

| 4,960,759 | A | 10/1990 | De Luca et al. |
| 2001/0056101 | A1* | 12/2001 | Tamminga et al. ........... 514/310 |
| 2004/0147613 | A1 | 7/2004 | Dawirs |
| 2010/0298382 | A1 | 11/2010 | Seeman et al. |

FOREIGN PATENT DOCUMENTS

| CA | 2628298 A | 11/2006 |
| CN | 1681491 A | 10/2005 |
| CN | 1802153 A | 7/2006 |
| RU | 2057529 C1 * | 4/1996 |
| WO | 2006047861 A1 | 5/2006 |

OTHER PUBLICATIONS

Seeman, P., et al., "Antipsychotic drugs which elicit little or no Parkinsonism bind more loosely that dopamine to bring D2 receptors, yet occupy high levels of these receptors", Molecular Psychiatry, vol. 3, No. 2, Mar. 1, 1998, pp. 123-134.
International Search Report and Written Opinion of PCT/CA2010/001185 dated Dec. 20, 2010.

* cited by examiner

*Primary Examiner* — Sreeni Padmanabhan
*Assistant Examiner* — Jody Karol
(74) *Attorney, Agent, or Firm* — Bereskin & Parr LLP/S.E.N.C.R.L.,s.r.l.; Patricia Folkins (57) ABSTRACT

This application describes compositions of receptor inhibitors, including typical antipsychotic agents, for example haloperidol, and methods of use for treating clinical signs or symptoms of Parkinson's disease. Furthermore, this application describes compositions and methods to induce supersensitivity in dopamine D2 and other receptors involved in Parkinson's disease as a means of alleviating the clinical signs or symptoms of Parkinson's disease.

9 Claims, 1 Drawing Sheet

COMPOSITIONS AND METHODS FOR TREATING PARKINSON'S DISEASE

RELATED APPLICATIONS

This application is a national phase entry of co-pending PCT patent application serial number PCT/CA2010/001185, filed Jul. 30, 2010, which claims priority from U.S. Provisional patent application Ser. No. 61/230,264 filed Jul. 31, 2009, each of these applications being incorporated herein by reference in their entirety.

FIELD OF THE APPLICATION

The present application relates to compositions of receptor inhibitors including antipsychotics such as haloperidol and methods for alleviating the clinical symptoms of Parkinson's disease. Furthermore, this application relates to methods of use of compositions of receptor inhibitors, including dopamine receptor inhibitors, to promote supersensitivity in receptors associated with Parkinson's disease as a means of alleviating the clinical symptoms of Parkinson's disease.

BACKGROUND OF THE APPLICATION

Parkinson's Disease

Parkinson's disease occurs in approximately one in 200 people during their lifetime. The disease may include hand and finger tremor, general akinesia, inability to get up from a chair, slow gait, stooped posture, expressionless face, constipation, among other symptoms.

Parkinson's disease is caused by a marked reduction in the content of dopamine in the brain, especially in the caudate nucleus and the putamen, regions important in regulating the control of arms, legs and body motion.

Types of Anti-Parkinson Medications

There are many types of anti-Parkinson medications used in clinical practice. These medications include:

1. L-DOPA taken orally. The L-DOPA enters the brain regions that are low in dopamine, and the L-DOPA is metabolized in those regions to produce dopamine. High doses of several grams per day of L-DOPA may be needed. Other medications can be taken simultaneously to minimize the metabolism of L-DOPA by other body tissues, thus providing higher concentrations of circulating L-DOPA.

2. Dopamine D2 receptor agonists, which include bromocriptine, apomorphine, N-propylnorapomorphine, pramipexole, cabergoline, pergolide, and quinagolide.

3. Many other medications affecting adenosine or cholinergic neurotransmission are also being examined for the alleviation of Parkinson's disease.

Use of Antipsychotics in Parkinson's Disease

In treating various psychoses, including schizophrenia, effective doses of antipsychotic drugs occupy between 60% and 80% of the dopamine D2 receptors in the brain striata of patients, as measured by PET or SPET in the human striatum. Clozapine and quetiapine, however, have consistently been apparent exceptions. For example, in patients taking therapeutically effective antipsychotic doses of clozapine, this drug only occupies between 0% and 50% of brain dopamine D2 receptors, as measured by a variety of radioligands using either positron tomography or single photon tomography.

Although the apparently low occupancy of D2 by clozapine might suggest that D2 is not the major antipsychotic target for clozapine, the apparently low occupancy of D2 by clozapine and quetiapine is readily explained by the fact that these two antipsychotics rapidly dissociate from the dopamine D2 receptor. This also holds for remoxipride and amisulpride, two atypical drugs. For example, human cloned dopamine D2 receptors release [$^3$H]clozapine, [$^3$H]quetiapine, [$^3$H]remoxipride and [$^3$H]amisulpride at least one hundred times faster than they release [$^3$H]haloperidol or [$^3$H]chlorpromazine.

These in vitro data match those found clinically for clozapine, quetiapine and haloperidol in schizophrenia patients and volunteers. For example, it has been found by PET (using [$^{11}$C]raclopride) that the human brain (striatum) occupancy of D2 by quetiapine and clozapine rapidly falls off within 24 hours, in contrast to that for haloperidol which maintains its D2 occupancy constant over 24 hours.

Thus, the rapid release of clozapine and quetiapine from dopamine D2 receptors and their replacement by endogenous dopamine would readily account for the low D2 receptor occupancy shown by these atypical antipsychotics. It is important to emphasize that the rapid release of clozapine and quetiapine is a molecular event which occurs quickly regardless of the clinical dose used. In other words, even though high doses of clozapine and quetiapine may be used in the patient, these drugs continue to go on and off the D2 receptor rapidly, allowing extensive and frequent access of endogenous dopamine to the receptor.

As outlined above, the "fast-off" theory of atypical antipsychotic action is that the atypicals have low affinities for the dopamine D2 receptor, and are loosely bound to, and rapidly released from, these receptors. A critical aspect of the theory is that the atypical antipsychotics bind more loosely to D2 than does dopamine itself, while the traditional, typical antipsychotics bind more tightly than dopamine.

The separation between typical and atypical antipsychotics is not sharp and precise, because antipsychotics with dissociation constants (K values) between 2 nM and 10 nM often reveal dose-dependent extrapyramidal signs. Thus, the demarcation between typical and atypical antipsychotics is not a sharp divide but rather a continuous one. Antipsychotics become increasingly more atypical as their binding to the D2 receptor becomes looser and they are released more quickly. Although many atypical antipsychotics have loose binding, with dissociation constants looser than 1.8 nM (nanomoles per liter), they can still elicit dose-dependent Parkinsonism. For example, olanzapine, with a dissociation constant of 5.1 nM, is known to be associated with a dose-dependent incidence of extrapyramidal signs in some patients and especially at higher doses. If the binding is extremely "loose," as with clozapine, remoxipride, quetiapine, and melperone, essentially no EPS occurs (although exquisitely sensitive patients do exist who will exhibit EPS even with these drugs). Drugs that are too "loose" or have far too low an affinity for D2 receptors cease to exhibit any antipsychotic activity at all. Moreover, although the degree of occupancy of atypicals at D2 receptors has a direct influence on EPS, the potent anticholinergic action of olanzapine and clozapine provides an additional anti-EPS mechanism.

L-DOPA Psychosis

The "Fast-off-D2" theory, described above, predicts low doses of atypical antipsychotics to alleviate L-DOPA psychosis. The treatment of patients with psychosis in Parkinson's disease (as a consequence of L-DOPA treatment) is best done with a very loose binding atypical antipsychotic, such as clozapine or quetiapine, to allow for the low level of dopamine neurotransmission that is required for normal motor functioning to continue. Parkinson patients are dopamine-depleted so it is generally important to not block the low level of dopamine function that remains. The hypothesis is that atypical antipsychotic action (i.e., low EPS) occurs when endogenous dopamine is able to displace a loosely bound antipsychotic. This is in accord with the observation that low doses of atypical antipsychotics are useful for Parkinson patients with L-DOPA psychosis.

L-DOPA psychosis in a Parkinson's diseased patient is best treated with a dose of clozapine which is about 10% of the dose normally used for treating psychosis in schizophrenia. The "fast-off-D2" hypothesis readily and quantitatively predicts this. As presented above, the antipsychotic dose needed to occupy D2 receptors is proportional to $K \times [1+D/D^{High}]$, where K is the dissociation constant of the antipsychotic, D is the concentration of dopamine in the synaptic space during the momentary nerve impulse (~200 nM), and where $D^{High}$ is the dissociation constant of dopamine at the high-affinity state of D2 (1.75 nM). In Parkinson's disease, where 90% to 95% of the dopamine content is absent, the value for D would be 20 nM. Accordingly, the antipsychotic dose for L-DOPA psychosis will be lower than that for schizophrenia psychosis by a factor of $\{1+D/D^{High}\}$normal$/\{1+D/D^{High}\}$Parkinson or $\{1+200/1.75\}/\{1+20/1.75\}$ or 10-fold (P. Seeman. Canad. J. Psychiat. 47: 27-38, 2002).

Thus, while a daily dose of 500 mg clozapine might be suitable for treating schizophrenia psychosis, a dose of 50 mg (or less) would be more than adequate to treat L-DOPA psychosis.

Haloperidol

Haloperidol is a first generation "typical" antipsychotic medication. Associated with this class of drugs are many side-effects. Using the customary daily doses of 5 to 20 mg of oral haloperidol per day on a long-term basis, the following are such side effects. Cardiovascular effects include: tachycardia, hypotension, and hypertension, QT prolongation and/or ventricular arrhythmias, ECG patterns indicating torsade de pointes, and sudden and unexpected death. Central nervous system effects include extrapyramidal signs (EPS) such as Parkinson-like signs, akathisia or dystonia (including opisthotonos and oculogyric crises), tardive dyskinesia and tardive dystonia. The following are other central nervous system effects associated with the use of standard antipsychotic doses of haloperidol: insomnia, restlessness, anxiety, euphoria, agitation, drowsiness, depression, lethargy, headache, confusion, vertigo, and grand mal seizures. Neuroleptic malignant syndrome (NMS), hyperpyrexia and heat stroke have been reported with haloperidol.

The following is a current list of indications for the use of haloperidol: acute psychosis, such as drug-induced psychosis (LSD, amphetamines, phencyclidine), acute mania, hyperactivity, aggression, agitation and confusion associated with cerebral sclerosis, adjunctive treatment of alcohol and opioid withdrawal, treatment of neurological disorders such as tics, Tourette syndrome, and chorea, treatment of severe nausea/emesis (postoperative, side-effects of radiation and cancer chemotherapy), adjunctive treatment of severe chronic pain, always together with analgesics, personality disorders such as borderline personality disorders and in the treatment of intractable hiccups.

SUMMARY OF THE APPLICATION

In the present application, it is shown that a low level of additional post-synaptic receptor supersensitivity, as controlled by an extremely low level of dopamine D2 receptor blockade such as to increase the level of receptors in the functional or "high affinity" state, can alleviate symptoms of Parkinson's disease.

The present application therefore includes a method of treating Parkinson's disease, comprising administering, to a subject in need thereof, an amount of a receptor inhibitor that is effective to elevate amounts of the high affinity state of the receptor, inducing receptor supersensitivity, wherein the receptor is associated with symptoms of Parkinson's disease.

In a further aspect, the method also includes stopping administration of the receptor inhibitor after receptor supersensitivity is induced, followed by restarting administration of the receptor inhibitor after a time sufficient for the induction of receptor supersensitivity to decrease and, optionally, repeating the stopping and restarting administration cycle for a period of time effective to treat the symptoms of Parkinson's disease.

The present application further includes a use of a receptor inhibitor to treat the symptoms of Parkinson's disease wherein said receptor inhibitor is used in an amount and for a time period that is effective to elevate amounts of the high affinity state of the receptor, inducing receptor supersensitivity, wherein the receptor is associated with symptoms of Parkinson's disease. In an embodiment, the use of the receptor inhibitor is stopped after receptor supersensitivity is induced, followed by restarting use of the receptor inhibitor after a time sufficient for the induction of receptor supersensitivity to decrease and, optionally, repeating the stopping and restarting cycle for a period of time effective to treat the symptoms of Parkinson's disease.

In an embodiment of the application, the subject is a Parkinson's patient being treated with effective amounts of a dopamine agonist.

In an embodiment of the application the receptor associated with symptoms of Parkinson's disease is the dopamine D2 receptor.

In an embodiment of the application, the amount of a dopamine D2 receptor inhibitor that is effective to elevate dopamine $D2^{High}$ receptor amounts, thereby inducing dopamine supersensitivity, is approximately one-hundredth to one tenth of the typical daily antipsychotic dose of the dopamine D2 receptor inhibitor.

The low dosage of the dopamine D2 receptor inhibitor would occupy of the order of 1% of the dopamine D2 receptors or less, thus avoiding any additional Parkinsonism or extrapyramidal motor reactions. This low level of dopamine supersensitivity is mediated by the dopamine D2 receptor inhibitor induction of an increase in the proportion of dopamine D2 receptors that are in the high-affinity state, or $D2^{High}$. The method of the present application is applicable to haloperidol and other antipsychotic agents and other receptors associated with symptoms of Parkinson's disease.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

BRIEF DESCRIPTION OF THE DRAWINGS

The present application will now be described in greater detail with reference to the drawings in which.

DETAILED DESCRIPTION OF THE APPLICATION

The present application describes the receptor supersensitivity action of a low dose of haloperidol which is based on its ability to elevate the proportion of dopamine D2 receptors that are in the high-affinity state. This results in increased psychomotor activity.

Although it is known that patients in early stages of Parkinson's disease may have low levels of dopamine D2 receptor supersensitivity, the concept here is that there is a clinical benefit to increase the level of this supersensitivity in order to alleviate the symptoms of the progression of Parkinson's disease. This is based on the principle that a low level of additional post-synaptic receptor supersensitivity, as controlled by an extremely low level of dopamine D2 receptor blockade (such as to increase the level of D2 receptors in the functional $D2^{High}$ or "high affinity" state) can alleviate symptoms of Parkinson's disease, for example, by significantly enhancing the daily action of a dopamine agonist. One embodiment of the present application, therefore, is to supplement the daily dopamine agonist dose with an extremely low dose of haloperidol in Parkinson patients. Preliminary data showed a reduction in symptoms, including an improvement in dyskinesia, using the Marinus scale (Marinus J, Visser M, Stiggelbout A M, Rabey J M, Martínez-Martín P, Bonuccelli U, Kraus P H, van Hilten J J. A short scale for the assessment of motor impairments and disabilities in Parkinson's disease: the SPES/SCOPA. J Neurol Neurosurg Psychiatry 75(3):388-395, 2004).

It has been found that all antipsychotic drugs block dopamine D2 receptors in direct relation to their standard doses of antipsychotic clinical potency (P. Seeman et al., PNAS, 1975).

The present application relates to novel and heretofore undisclosed compositions and methods to produce controlled receptor supersensitivity with unusually low toxicity for the treatment of symptoms of Parkinson's disease.

The present application includes a method of treating the symptoms of Parkinson's disease, comprising administering, to a subject in need thereof, an amount of a receptor inhibitor that is effective to elevate amounts of the high affinity state of the receptor, inducing receptor supersensitivity, wherein the receptor is associated with symptoms of Parkinson's disease.

In a further aspect, the method also includes stopping administration of the receptor inhibitor after receptor supersensitivity is induced, followed by restarting administration of the receptor inhibitor after a time sufficient for the induction of receptor supersensitivity to begin to decrease and, optionally, repeating the stopping and restarting administration cycle for a period of time effective to treat the symptoms of Parkinson's disease. "Stopping administration of the receptor inhibitor" includes cessation of administration or use of the compound or substitution of the administration or use of the compound with administration or use of a placebo.

In an embodiment of the application, the subject is a Parkinson's patient being treated with effective amounts of a dopamine agonist. In further embodiment, the dopamine agonist is one that is known to be useful for treating Parkinson's Disease, for example, but not limited to, L-DOPA, Sinemet, bromocriptine and pramipexole.

The present application further includes a use of a receptor inhibitor to treat the symptoms of Parkinson's disease, wherein said receptor inhibitor is used in an amount and for a time period that is effective to elevate amounts of the high affinity state of the receptor, inducing receptor supersensitivity. In an embodiment, the use of the receptor inhibitor is stopped after receptor supersensitivity is induced, followed by restarting use of the receptor inhibitor after a time sufficient for the induction of receptor supersensitivity to begin to decrease and, optionally, repeating the stopping and restarting cycle for a period of time effective to treat the symptoms of Parkinson's disease.

In another embodiment of the application, the receptor inhibitor is used, or is formulated for use, in combination with a dopamine agonist. In further embodiment, the dopamine agonist is one that is known to be useful for treating Parkinson's Disease, for example, but not limited to, L-DOPA, Sinemet, bromocriptine and pramipexole.

Compounds that induce receptor supersensitivity are also known in the art. To "induce receptor supersensitivity" refers to compounds that can produce an increased number or elevated density or amount of receptors in the high affinity state in a subject's brain, in particular compared to control levels.

By "increase" it is meant any detectable elevation in a variable, for example amount of receptors in the high affinity state in a subject's brain.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The symptoms of Parkinson's disease are known in the art and include, but are not limited to:

Primary Symptoms:

Bradykinesia: slowness in voluntary movement. It produces difficulty initiating movement, as well as difficulty completing movement once it is in progress. The delayed transmission of signals from the brain to the skeletal muscles, due to diminished dopamine, produces bradykinesia. Bradykinesia and rigidity that affects the facial muscles can result in an expressionless, "mask-like" appearance.

Tremors: in the hands, fingers, forearm, or foot tend to occur when the limb is at rest, but not when the patient is performing tasks. Tremor may occur in the mouth and chin as well.

Rigidity: or stiff muscles, may produce muscle pain and facial masking. Rigidity tends to increase during movement.

Poor balance: is due to the impairment or loss of the reflexes that adjust posture in order to maintain balance. Falls are common in people with Parkinson's disease.

Parkinsonian gait: is the distinctive unsteady walk associated with Parkinson's disease. There is a tendency to lean unnaturally backward or forward, and to develop a stooped, head-down, shoulders-drooped stance. Arm swing is diminished or absent and people with Parkinson's tend to take small shuffling steps (called festination). Patient's with Parkinson's may have trouble starting to walk, may appear to be falling forward as they walk, may freeze in mid-stride, and may have difficulty making a turn.

Secondary Symptoms

The progressive loss of voluntary and involuntary muscle control produces a number of secondary symptoms associated with Parkinson's. Most patients do not experience all of them, and symptoms vary in intensity from person to person.

Some secondary symptoms of Parkinson's disease include the following:
   Constipation
   Depression
   Difficulty swallowing (dysphagia)-saliva and food may collect in the mouth or back of the throat may cause choking, coughing, or drooling
   Excessive salivation (hypersalivation)
   Excessive sweating (hyperhidrosis)
   Loss of intellectual capacity (dementia)-late in the disease
   Psychosocial: anxiety, depression, isolation
   Scaling, dry skin on the face and scalp (seborrhea)
   Slow response to questions (bradyphrenia)
   Small, cramped handwriting (micrographia)
   Soft, whispery voice (hypophonia)

The symptoms of Parkinson's disease can be rated, for example, using the Marinus scale (Marinus J, Visser M, Stiggelbout A M, Rabey J M, Martínez-Martín P, Bonuccelli U, Kraus P H, van Hilten J J. A short scale for the assessment of motor impairments and disabilities in Parkinson's disease: the SPES/SCOPA. J Neurol Neurosurg Psychiatry 75(3):388-395, 2004).

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with the symptoms of Parkinson's disease.

The term "subject" or "patient" or synonym thereto, as used herein includes all members of the animal kingdom, especially mammals, including human. The subject or patient is suitably a human.

In an embodiment of the application the receptor inhibitor is a dopamine receptor inhibitor. In a further embodiment of the application the receptor inhibitor is a dopamine D2 receptor inhibitor.

In an embodiment of the present application, the dopamine D2 receptor inhibitor used to stimulate supersensitivity in the dopamine D2 receptor is a typical antipsychotic agents including, but not limited to, haloperidol, chlorpromazine, fluphenazine, molindone, thiothixine, thioridazine, trifluoperazine, loxapine, perphenazine, prochloroperazine, pimozide, and zuclopenthixol. In a further embodiment, the dopamine D2 receptor inhibitor is haloperidol.

In a further embodiment of the present application the amount of a dopamine D2 receptor inhibitor that is effective to elevate dopamine $D2^{High}$ receptor amounts, inducing dopamine supersensitivity, are those doses which result in dopamine D2 supersensitivity and/or reduced symptoms of Parkinson's disease.

While it is understood that dopamine D2 receptor inhibitors have different potencies and dose should be adjusted according to the potency, it is an embodiment of the disclosure that doses may be between approximately one-hundredth to one-tenth, one-eightieth to one-twentieth, one-sixtieth to one-fortieth, or one fiftieth of the typical daily antipsychotic dose of the agent or an amount to achieve a receptor occupancy of the dopamine D2 receptor of about 1% or 2%. In another embodiment of the disclosure, oral preparations of low-dose haloperidol for example, may be formulated, suitably as tablets, capsules, or drops, containing about 0.005-1.0 milligrams, about 0.01-0.5 milligrams, about 0.025-0.1 milligrams, 0.025-0.045 milligrams or about 0.040 milligrams of haloperidol, per dosage unit. The compounds described herein may be administered initially in a suitable dosage that may be adjusted as required, depending on the clinical response.

In another embodiment of the present application, dose scheduling to be used to result in dopamine D2 supersensitivity is to be determined as those schedules which, in combination with appropriate dose, results in dopamine D2 supersensitivity. Dose schedules are expected to be altered according to the specific dopamine D2 receptor inhibitors used to maximize the clinical effects.

In an embodiment, the administration or use of the dopamine D2 receptor inhibitor comprises a daily use or administration of the effective amount of the dopamine D2 receptor inhibitor for 3 to 20 days, 4 to 19 days, 5 to 18 days, 6 to 17 days, 7 to 16 days, 8 to 15 days or 9 to 14 days.

As noted above, the administration or use of the dopamine D2 receptor inhibitor may be stopped after dopamine supersensitivity is induced, followed by restarting administration of the dopamine D2 receptor inhibitor after a time sufficient for the induction of dopamine supersensitivity to begin to decrease and, optionally, repeating the stopping and restarting administration cycle for a period of time effective to treat the symptoms of Parkinson's disease. Examples of dose schedules include, but are not limited to: about 3 days to about 20 days, suitably about 3 days to about 10 days, more suitably about 3 days to about 7 days, dosing with active dopamine D2 receptor inhibitor followed by about 3 days to about 20 days, suitably about 3 days to about 10 days, more suitably about 3 days to about 7 days of no dopamine D2 receptor inhibitor or of placebo and repeating this cycle of active dopamine receptor inhibitor and placebo, as needed.

Accordingly, in one embodiment, the method of the application comprises
   (a) administering for about 3 days to about 20 days, suitably about 3 days to about 10 days, more suitably about 3 days to about 7 days, a low dose of dopamine D2 receptor inhibitor followed by about 3 days to about 20 days, suitably about 3 days to about 10 days, more suitably about 3 days to about 7 days, of no dopamine D2-receptor inhibitor or of placebo; and
   (b) optionally repeating (a) for a period of time effective to treat the clinical symptoms of Parkinson's disease.

In this embodiment, the term "low dose" means about 0.005 mg to about 0.05 mg, about 0.01 to about 0.050 mg or about 0.040 mg per day, suitably in a single dose. These combinations of low doses of antipsychotic agent and novel dose-schedules result in sustained supersensitivity associated with increasing the proportion of dopamine D2 receptors in the high-affinity state. This sustained increase in the proportion of dopamine D2 receptors in the high-affinity state would expect to result in anti-Parkinsonian activity through sensitizing the post-synaptic receptors to endogenous dopamine.

In alternate embodiment, the dosing schedule includes administration of higher amounts of dopamine D2 receptor inhibitor on alternate days for a period of about 7 days to about 20 days, suitably about 7 days to about 10 days, followed by about 7 days to about 20 days of no dopamine D2 receptor inhibitor or placebo and repeating this cycle of alternate day active dopamine receptor inhibitor and no dopamine D2 receptor inhibitor or placebo, as needed.

Accordingly, in another embodiment, the method of the application comprises
   (a) administering on alternate days for about 7 days to about 20 days, suitably about 7 days to about 10 days, of a high dose of dopamine D2 receptor inhibitor followed by about 7 days to about 20 days, suitably about 7 days to about 10 days, of no dopamine D2-receptor inhibitor or of placebo; and (c) optionally repeating (a) for a period of time effective to treat the clinical symptoms of Parkinson's disease.

In this embodiment, the term "high dose" means about 0.1 mg to about 1.0 mg, suitably about 0.5 mg per day, suitably in single or divided doses. The term "alternate days" means every other day.

The term "about" in reference to numbers of days means +/−1-5 days, suitably +/−3 days.

In animals, an increase in dopamine $D2^{High}$ leads to hyperactivity (P. Seeman et al., PNAS Mar. 1, 2005), one of the indicators of a motor-activating effect.

Low dose haloperidol and low doses of other antipsychotics have not been used clinically to alleviate the symptoms of Parkinson's disease, other than their use in suppressing the symptoms of psychosis caused by L-DOPA or the other dopamine D2 agonists.

As used herein, the term "receptor supersensitivity" refers to an enhanced response to the stimulation of the dopamine D2 receptor by endogenous dopamine or another exogenously administered dopamine receptor agonist medication, previously mentioned. The D2 receptor, which is linked to a G protein (of which there are many types), can exist in two states. One state has a high affinity for the receptor agonist, dopamine, with a dissociation constant of 1.5 nM for the D2 receptor, for example, and this state is referred to as the high-affinity state, or $D2^{High}$. The other state has a low affinity for the neurotransmitter, dopamine, with a dissociation constant of approximately 200-2000 nM for the D2 receptor, for example, and this state is referred to as the low-affinity state, or $D2^{Low}$. Depending on local conditions in vitro or in vivo, the two states can quickly convert into each other. Because the high-affinity state is considered the functional state (S. R. George et al., Endocrinology 117: 690, 1985), the process of "desensitization" occurs whenever the high-affinity state converts into the low-affinity state.

Although the commonly used antipsychotic dosage of haloperidol is between and 20 mg per day (oral dose), the present method advocates a dose of about 0.005 mg to about 0.5 mg, about 0.01 mg to about 0.1 mg, about 0.025 mg to about 0.05 mg, (oral) given each day for approximately 10 to 20 days. The dosage may either be maintained or stopped for about a week and re-started about one or two weeks later, depending on the clinical state of the patient. These doses and dosing regimens are by way of example and not limitation.

The receptor inhibitors, including haloperidol, may be used in any pharmaceutically acceptable form, including salts, solvates and prodrugs thereof.

The term "pharmaceutically acceptable" means compatible with the treatment of animals, in particular, humans.

The term "pharmaceutically acceptable salt" means an acid addition salt or a basic addition salt which is suitable for or compatible with the treatment of patients.

The term "pharmaceutically acceptable acid addition salt" as used herein means any non-toxic organic or inorganic salt of any base compound. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

The term "pharmaceutically acceptable basic addition salt" as used herein means any non-toxic organic or inorganic base addition salt of any acid compound. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound, or a pharmaceutically acceptable salt of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds will vary depending on the compound and the solvate. In general, solvates are formed by dissolving the compound in the appropriate solvent and isolating the solvate by cooling or using an antisolvent. The solvate is typically dried or azeotroped under ambient conditions.

The present application includes within its scope, the use of prodrugs of the receptor inhibitors. In general, such prodrugs will be functional derivatives of a compound which are readily convertible in vivo into the compound from which it is notionally derived. Prodrugs may be conventional esters formed with available hydroxy, or amino group. For example, an available OH or NH group in a compound may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In further embodiments, the prodrugs are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

The receptor inhibitor is suitably formulated into pharmaceutical compositions for administration to human subjects in a biologically compatible form suitable for administration in vivo.

The compositions described herein can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

In accordance with the methods of the use application, the described compounds, salts or solvates thereof may be administered to a patient in a variety of forms depending on the selected route of administration, as will be understood by those skilled in the art. The compositions of the application may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

Compounds described herein may be orally administered, for example, with an inert diluent or with an assimilable edible carrier, or may be enclosed in hard or soft shell gelatin capsules, or may be compressed into tablets, or may be incorporated directly with the food of the diet. For oral therapeutic administration, the compounds may be incorporated with excipient and used in the form of ingestible tablets, buccal tablets, troches, capsules, elixirs, suspensions, syrups, wafers, and the like.

Compounds described herein may also be administered parenterally. Solutions can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990-18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists. Ampoules are convenient unit dosages.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compositions for topical administration may include, for example, propylene glycol, isopropyl alcohol, mineral oil and glycerin. Preparations suitable for topical administration include liquid or semi-liquid preparations such as liniments, lotions, applicants, oil-in-water or water-in-oil emulsions such as creams, ointments or pastes; or solutions or suspensions such as drops; or solid controlled release forms such as transdermal patches. In addition to the aforementioned ingredients, the topical preparations may include one or more additional ingredients such as diluents, buffers, flavouring agents, binders, surface active agents, thickeners, lubricants, preservatives, e.g. methyl hydroxybenzoate (including antioxidants), emulsifying agents and the like.

Sustained or direct release compositions can be formulated, e.g. liposomes or those wherein the active compound is protected with differentially degradable coatings, such as by microencapsulation, multiple coatings, etc. It is also possible to freeze-dry the compounds of the application and use the lypolizates obtained, for example, for the preparation of products for injection.

The compounds may be administered to a subject alone or in combination with pharmaceutically acceptable carriers, as noted above, the proportion of which is determined by the solubility and chemical nature of the compound, chosen route of administration and standard pharmaceutical practice.

The dosage of the compounds and/or compositions described herein can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors and the teachings in the present application.

Oral preparations of low-dose haloperidol may be formulated, suitably as tablets, capsules, or drops, containing about 0.005-1.0 milligrams, suitably about 0.01-0.5 milligrams, more suitably 0.025-0.1 milligrams, more suitably 0.025-0.05 milligrams, of haloperidol described herein, per dosage unit. The compounds described herein may be administered initially in a suitable dosage that may be adjusted as required, depending on the clinical response.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately", unless otherwise indicated as used herein mean a reasonable amount of deviation of the modified term such that the end result is not significantly changed. These terms of degree should be construed as including a deviation of at least ±5% of the modified term if this deviation would not negate the meaning of the word it modifies.

EXAMPLES

Example 1

Administration of Low Dose Haloperidol to Rats

The customary dose of haloperidol in treating psychosis in humans is between mg/day and 20 mg/day on a continuing basis. These therapeutic doses are known to occupy between 60% and 70% of dopamine D2 receptors in the human brain, as revealed by positron emission tomography. In the rat, the human dose of 5-20 mg/day of haloperidol corresponds to 0.04-08 mg/kg (S. Kapur, S. C. Vanderspek, B. A. Brownlee, J. N. Nobrega, Antipsychotic dosing in preclinical models is often unrepresentative of the clinical condition: A suggested solution based on in vivo occupancy. J. Pharmacol. Exper. Therap. 305: 625-631, 2003).

Figure 1:
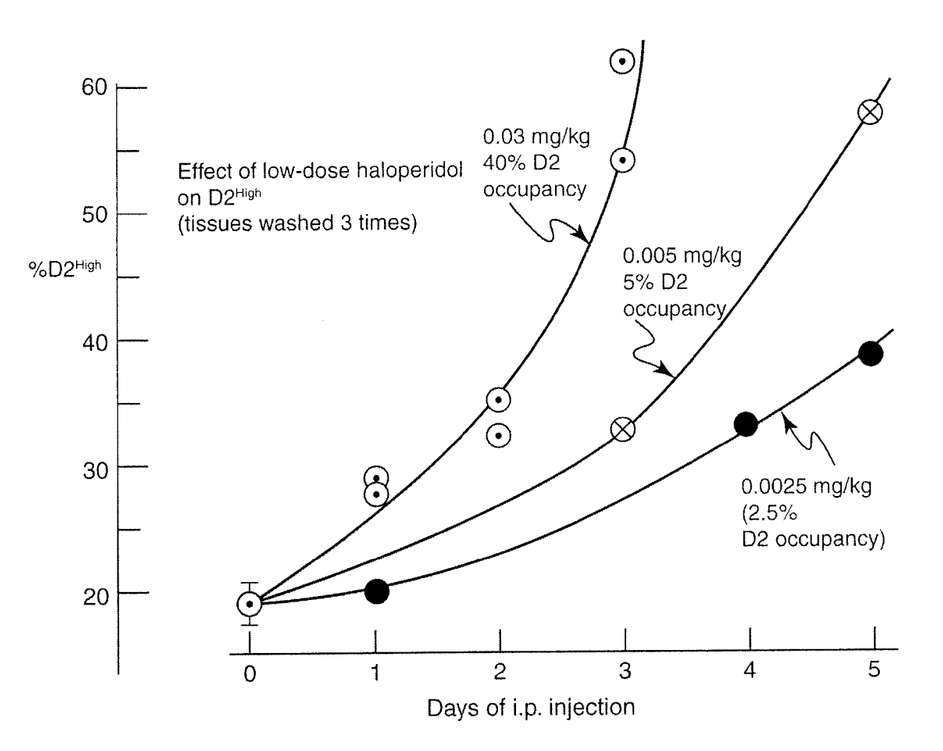
FIG. 1 is a graph showing the effect of low-dose haloperidol on $D2^{High}$ levels.

However, a surprising finding was that using haloperidol doses in rats of 0.03 mg/kg down to 0.0025 mg/kg, which are much lower than those used clinically, results in levels or proportions of $D2^{High}$ receptors that were moderately elevated by 30% or 40%. Such animals exhibited heightened locomotion and active exploration analogous to increased curiosity and increased well-being in humans. For example, the data in FIG. 1 shows that 0.0025 mg/kg/day of haloperidol (i.p.) in rats elicited a 30-40% increase of $D2^{High}$ receptors between 4 and 5 days. Specifically it was found that 0.0025 mg/kg/day increased $D2^{High}$ by 38% in 5 days, with the animals showing heightened locomotion, active exploration and good grooming.

The data in the FIG. 1 illustrate that a very low dose of haloperidol, 0.005 mg/kg, elevates $D2^{High}$ receptors approximately two-fold over a matter of 3-5 days. On days 3-5 or upon stopping the haloperidol, these rats showed spontaneously increased locomotion and well-being insofar as they groomed themselves more actively as well as being more spontaneously active. These data indicate that low-dose haloperidol has the effect of elevating the levels of $D2^{High}$ receptors in rats and the assay can be used to assess other agents for their ability to elevate $D2^{High}$ levels in animals.

Example 2

Competitive Binding Assays

The method for measuring the proportion of D2 receptors in the high-affinity state is as follows. (The general method is also used for measuring the competitive potency of a compound at any particular receptor).

After $CO_2$ euthanasia, rat brains are immediately removed, and the striata dissected and frozen at $-80°$ C. until used. The striata are homogenized in buffer (4 mg frozen striatum per ml buffer consisting of 50 mM Tris-HCl [pH 7.4 at 20° C.], 1 mM EDTA, 5 mM KCl, 1.5 mM $CaCl_2$, 4 mM $MgCl_2$; 120 mM NaCl), using a Teflon-glass homogenizer, with the piston rotating at 500 rpm, and 10 up and down strokes of the glass container. The homogenate is not washed because it is known that 30-50% of the D2 receptors can be lost by this procedure.

[$^3$H]Domperidone is custom synthesized as [phenyl-$^3$H (N)]domperidone (42-68 Ci/mmol) by PerkinElmer Life Sciences Inc., Boston, Mass., and used at a final concentration of 2 nM. The dissociation constant, Kd, for [$^3$H]domperidone is 0.47 nM at dopamine D2 receptors in rat striatum.

The proportion of $D2^{High}$ receptors in the striata is measured by the competition of dopamine with 2 nM [$^3$H]domperidone, as follows. Each incubation tube (12×75 mm, glass) receives, in the following order, 0.5 ml buffer (containing dopamine at various concentrations, with or without a final concentration of 10 μM S-sulpiride to define nonspecific binding to the dopamine D2 receptors), 0.25 ml [$^3$H]domperidone, and 0.25 ml of the striatal homogenate. The tubes, containing a final volume of 1 ml, are incubated for 2 h at room temperature (20° C.), after which the incubates are filtered, using a 12-well cell harvester (Titertek, Skatron, Lier, Norway) and buffer-presoaked glass fiber filter mats (Whatman GF/C). After filtering the incubate, the filter mat is rinsed with buffer for 15 s (7.5 ml buffer). The filters are pushed out and placed in scintillation polystyrene minivials (7 ml, 16×54 mm; Valley Container Inc., Bridgeport, Conn.). The minivials receive 4 ml each of scintillant (Research Products International Corp., Mount Prospect, Ill.), and are monitored 6 h later for tritium in a Beckman LS5000TA scintillation spectrometer at 55% efficiency. The specific binding of 2 nM [$^3$H] domperidone is defined as total binding minus that in the presence of 10 μM S-sulpiride. The high-affinity phase occurs between 1 and 100 nM dopamine, while the low-affinity phase occurs between 100 and 10,000 nM dopamine. The two phases are clearly and consistently demarcated, not requiring computer-assisted resolution of the data into high- and low-affinity components. Moreover, the proportion of D2 receptors in the high-affinity phase between experiments is very consistent, further obviating the need for computer-assisted analysis.

The Cheng-Prusoff equation (Cheng and Prusoff, 1973) is used to derive the dissociation constant (Ki value) of dopamine from the concentration that inhibited 50% of the high-affinity component ($IC_{50}$) or 50% of the low-affinity component in the dopamine/[$^3$H]domperidone competition curve. The form of the Cheng-Prusoff equation used was $Ki=IC_{50}/(1+C/Kd)$, where C was the final concentration of the ligand and Kd was the dissociation constant of [$^3$H]domperidone, as determined directly by independent experiments of saturation binding to the tissue (i.e., Scatchard plot).

Although cloned receptors are used for the studying the properties of receptors other than D2, rat brain tissues are used to examine the high-affinity states of receptors.

The compound dissociation constant, K, is calculated as usual as $C50\%/[1+C^*/Kd]$, where $C50\%$ is the drug concentration which inhibits ligand binding by 50%, where $C^*$ is the ligand concentration, and where Kd is the dissociation constant of the ligand, as obtained from a separate experiment using a range of ligand concentrations.

Using the in vitro method outlined above, the Ki value of haloperidol at the dopamine D2 receptor was 0.7 nM.

The fraction of D2 receptors occupied, f, is given by $f=C/(C+Ki)$, where C is concentration of haloperidol in the plasma water or spinal water in a treated patient, and where Ki is the dissociation constant of haloperidol, 0.7 nM, at the D2 receptor.

When using low-dose haloperidol, say 0.001 mg/kg per day in humans, the plasma water concentration of haloperidol is expected to be one-hundredth of the usual concentration that elicits antipsychotic action, namely 1.5 nM in plasma water or spinal fluid water.

Therefore, at a dose of 0.001 mg/kg haloperidol per day, the fraction of D2 receptors expected to be occupied would be 0.01 nM/(0.01 nM+0.7 nM) or ~1.4%.

Therefore, the present proposed use of low-dose haloperidol would occupy approximately 1% of D2 receptors, not sufficient to elicit Parkinsonian symptoms but sufficient to elicit D2 supersensitivity and motor activation, in accord with FIG. 1, where each point is an average for two rats that received the haloperidol doses indicated (i.p.). Ordinate indicates the proportion of dopamine D2 receptors in the homogenized striata in the high-affinity state, using the method of dopamine competition with [$^3$H]domperidone. Nonspecific binding defined by 10 M S-sulpiride.

Example 3

Human Study

A low level of additional post-synaptic receptor supersensitivity, as controlled by an extremely low level of dopamine D2 receptor blockade (such as to increase the level of D2 receptors in the functional D2$^{High}$ or "high affinity" state) can alleviate symptoms of Parkinson's disease by significantly enhancing the daily action of a dopamine agonist. The objective in the present example, therefore, is to supplement the daily dopamine agonist dose with an extremely low dose of haloperidol in a small series of Parkinson patients. Data in one human showed at least a 30% to 40% reduction in symptoms, including an improvement in dyskinesia, using the Marinus scale (Marinus J, Visser M, Stiggelbout A M, Rabey J M, Martínez-Martín P, Bonuccelli U, Kraus P H, van Hilten J J. A short scale for the assessment of motor impairments and disabilities in Parkinson's disease: the SPES/SCOPA. J Neurol Neurosurg Psychiatry 75(3):388-395, 2004).

Methods: A Parkinson patient was tested to see whether a fourteen-day trial of a very low dose of haloperidol, added to their daily dose of dopamine agonist, enhances their motor signs and improves their mood symptoms.
Inclusion criteria: Parkinson patients who are taking a daily dose (or doses) of a dopamine agonist, including L-DOPA, Sinemet, bromocriptine, or pramipexole.
Exclusion criteria: Patients having additional major illnesses, such as cardiac illness.
Daily haloperidol dose: 40 micrograms in a capsule in AM. This dose is expected to occupy 1-2% of D2 receptors, not sufficient to enhance Parkinsonian symptoms but sufficient to elicit D2 supersensitivity and motor activation. A summary of the study protocol is as follows:
On first day, the patient's Parkinson's Disease (PD) is rated, followed by an oral dose of 40 micrograms haloperidol (H) added to the patient's regular medicine for PD.
On second day: no rating, just take 40 micrograms H
On third day: no rating, just take 40 micrograms H
On fourth day: no rating, just take 40 micrograms H
On fifth day: no rating, just take 40 micrograms H
On 6th day: no rating, just take 40 micrograms H
On 7th day: Rate patient's PD, followed by 40 micrograms H
On 8th day: no rating, just take 40 micrograms H
On 9th day: no rating, just take 40 micrograms H
On 10th day: no rating, just take 40 micrograms H
On 11th day: no rating, just take 40 micrograms H
On 12th day: no rating, just take 40 micrograms H
On 13th day: no rating, just take 40 micrograms H
On 14th day: Rate patient's PD. No further H.
If at any time the patient gets more stiffness with H, then the H dosing is stopped.
No placebo subjects needed at this time. Each patient was their own control, as rated on Day 1.
Assessment of Parkinson signs/symptoms: The short scale (SPES/SCOPA scale) by Marinus (ibid) was used. Patients were assessed at baseline and at end of the trial. At the end of trial, a statistical comparison was made between the baseline scores and the scores at the end of the trial.
Results:
At time 1 and 2, patient appeared brighter, less flat facial features. Also at time 1 and 2, patient walked faster with more confidence and could not be pushed over. Slight increase in rigidity on palpation of elbow joint on right side (no rigidity on left, either baseline or time 1 and 2). No involuntary movements noted at Time 1 or Time 2, apart from resting tremor of right hand which was present at all times.
Overall conclusion: A slight improvement from baseline to Time 1 and 2 on certain markers was observed, the most noticeable was walking and his overall presentation, i.e. he was less flat. Results are summarized in Table 1.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Data Chart for Parkinson's Study

| Motor Function Item | Baseline Time 1 | Score Time 2 | Score Time 3 |
|---|---|---|---|
| Rest Tremor | 2 | 2 | 2 |
| Postural Tremor | 1 | 1 | 1 |
| Alternating Movements | 1 | 0 | 1 |
| Rigidity | 1 | 2 | 2 |
| Rise from Chair | 0 | 0 | 0 |
| Postural stability | 0 | 0 | 0 |
| Gait | 1 | 0 | 1 |
| Speech | 1 | 0 | 0 |
| Freezing during "on" | 0 | 0 | 0 |
| Swallowing | 1 | 0 | 0 |
| ADL Speech | 1 | 0 | 0 |
| Feeding | 1 | 1 | 1 |
| Dressing | 1 | 1 | 1 |
| Hygiene | 1 | 1 | 1 |
| Changing position, i.e. turning in bed | 1 | 1 | 1 |
| Walking | 1 | 0 | 0 |
| Handwriting | 1 | 1 | 1 |
| Dyskinesias (presence) | 1 | 0 | 0 |
| Dyskinesias (severity) | 1 | 0 | 0 |
| Motor Fluctuations (presence) | 0 | 0 | 0 |
| Motor Fluctuations (severity) | 0 | 0 | 0 |

The invention claimed is:

1. A method of treating Parkinson's disease and/or symptoms caused by Parkinson's disease, comprising administering, to a subject in need thereof, an amount of a haloperidol that is effective to elevate amounts of the high affinity state of the D2 receptor, inducing D2 receptor supersensitivity, wherein the amount of haloperidol is daily administration of about 0.005 mg to about 0.05 mg, for 3 to 20 days.

2. The method according to claim 1, further comprising stopping administration of haloperidol after D2 receptor supersensitivity is induced, followed by restarting administration of haloperidol after a time sufficient for the induction of D2 receptor supersensitivity to begin to decrease and, optionally, repeating the stopping and restarting administration cycle for a period of time effective to treat Parkinson's disease.

3. The method according to claim 1, wherein dopamine D2 receptor occupancy of haloperidol after administering the amount that is effective to elevate amounts of the high affinity state of the dopamine D2 receptor, inducing dopamine D2 receptor supersensitivity, is about 1% or 2%.

4. The method according to claim 1, comprising
(a) administering for about 3 days to about 20 days, about 3 days to about 10 days, or about 3 days to about 7 days, haloperidol followed by about 3 days to about 20 days, about 3 days to about 10 days, or about 3 days to about 7 days, of no dopamine D2-receptor inhibitor or of a placebo; and
(c) optionally repeating (a) for a period of time effective to treat Parkinson's disease and/or the symptoms of Parkinson's disease.

5. The method according to claim 4, wherein the amount of haloperidol is about 0.01 to about 0.05 mg per day.

6. The method according to claim 4, wherein the symptoms caused by Parkinson's disease are selected from bradykinesia, tremors, rigidity, poor balance, Parkinsonian gait, constipation, depression, dysphagia, hypersalivation, hyperhidrosis, loss of intellectual capacity, anxiety, seborrhea, bradyphrenia, micrographia and hypophonia.

7. The method according to claim 6, wherein the symptoms caused by Parkinson's disease are loss of intellectual capacity.

8. The method according to claim 1, wherein the amount of haloperidol is about 0.025 mg to about 0.045 mg per day.

9. The method according to claim 1, wherein the amount of haloperidol is about 0.040 mg per day.

* * * * *